United States Patent
Dally

(10) Patent No.: US 12,414,658 B2
(45) Date of Patent: Sep. 16, 2025

(54) TOUCHLESS GLOVE APPLICATION SYSTEMS

(71) Applicant: James Edwin Dally, Kalamazoo, MI (US)

(72) Inventor: James Edwin Dally, Kalamazoo, MI (US)

( * ) Notice: Subject to any disclaimer, the term of this patent is extended or adjusted under 35 U.S.C. 154(b) by 61 days.

(21) Appl. No.: 17/827,348

(22) Filed: May 27, 2022

(65) Prior Publication Data

US 2022/0296051 A1 Sep. 22, 2022

Related U.S. Application Data

(62) Division of application No. 17/159,274, filed on Jan. 27, 2021, now Pat. No. 11,350,801.

(51) Int. Cl.
*A47K 10/42* (2006.01)
*A47G 25/90* (2006.01)
*A61B 42/50* (2016.01)

(52) U.S. Cl.
CPC ............ *A47K 10/42* (2013.01); *A47G 25/904* (2013.01); *A61B 42/50* (2016.02)

(58) Field of Classification Search
CPC ........ A47G 25/904; A61B 42/40; A61B 42/50
See application file for complete search history.

(56) References Cited

U.S. PATENT DOCUMENTS

| | | | | |
|---|---|---|---|---|
| 3,798,870 A * | 3/1974 | Kanner | ...................... | B65B 9/14 53/567 |
| 4,773,532 A * | 9/1988 | Stephenson | ........ | B65D 83/0811 206/390 |
| 4,889,266 A * | 12/1989 | Wight | .................... | A61B 42/40 223/111 |
| 4,909,413 A * | 3/1990 | McCutcheon | ....... | A47G 25/904 221/25 |
| 5,878,909 A * | 3/1999 | Rogow | .................. | A61B 42/50 221/45 |
| 6,375,034 B1 * | 4/2002 | Corbett | .................. | A61B 42/50 221/45 |
| 6,820,753 B2 * | 11/2004 | Kurtz | ..................... | A47K 10/20 211/49.1 |
| 7,588,168 B2 * | 9/2009 | Bagwell | ................. | A61B 42/40 221/96 |
| 7,635,067 B1 * | 12/2009 | Flynn | ..................... | A61B 42/40 223/111 |
| 8,146,776 B2 * | 4/2012 | Balkin | .................. | A47K 10/32 221/277 |

(Continued)

*Primary Examiner* — F Griffin Hall
(74) *Attorney, Agent, or Firm* — Vorys, Sater, Seymour and Pease LLP

(57) ABSTRACT

A glove application system includes a mounting bracket that provides an access aperture, and a glove cartridge assembly mountable to the mounting bracket and including a cartridge belt having a plurality of glove cartridges spaced along the cartridge belt, each glove cartridge having a glove releasably secured to the cartridge belt with a fastening system. The glove cartridge assembly is operable to advance the cartridge belt and sequentially align each glove cartridge with the access aperture. Extending a hand through the access aperture installs a glove from an aligned glove cartridge on the hand and simultaneously releases the glove from the cartridge belt.

12 Claims, 5 Drawing Sheets

(56) References Cited

U.S. PATENT DOCUMENTS

| | | | | |
|---|---|---|---|---|
| 8,678,252 | B2* | 3/2014 | Kelly | A61B 42/40 |
| | | | | 223/111 |
| 8,807,402 | B2* | 8/2014 | Backhaus | A41D 19/0072 |
| | | | | 223/111 |
| 9,295,352 | B2* | 3/2016 | Williams | A61B 42/10 |
| 9,624,027 | B2* | 4/2017 | DeGraaf | B65D 25/005 |
| D809,318 | S* | 2/2018 | Hammons | D6/515 |
| 10,098,699 | B1* | 10/2018 | Buck | A61B 42/40 |
| 10,321,725 | B2* | 6/2019 | Kantrowitz | A61B 42/40 |
| 11,324,562 | B2* | 5/2022 | Moghadam | A61B 42/50 |
| 2011/0186589 | A1* | 8/2011 | Lee | A61B 42/50 |
| | | | | 221/36 |
| 2022/0233008 | A1* | 7/2022 | Waineo | A47G 25/904 |

* cited by examiner

TOUCHLESS GLOVE APPLICATION SYSTEMS

BACKGROUND

The use of disposable gloves (e.g., latex gloves, nitrile gloves, etc.) is commonplace in many industries, and is generally recognized as one of the primary safeguards against inadvertent or accidental cross-contamination between a user (wearer) and the surrounding environment. When used properly, gloves improve hygiene and can minimize exposure for both the user and others, especially those serviced by the person wearing the gloves.

However, common errors that occur during glove application (placement) can compromise the overall effectiveness of glove use, such as allowing the exterior of the gloves to undergo significant physical contact prior to and during application. For example, gloves are commonly packaged in a manner that increases the probability that a user will physically contact multiple gloves with bare hands upon extracting a single glove. Moreover, the first glove is typically applied with a non-gloved hand, thereby possibly contaminating the exterior of the first glove. In effect, simply putting disposable gloves on manually can inadvertently contaminate multiple gloves intended for sterile or sanitary applications. Moreover, gloves can be contaminated through inadvertent or intentional contact with non-sanitary surfaces prior to the intended use.

Furthermore, in view of the COVID-19 pandemic that currently plagues our world, the use of disposable gloves has exponentially increased. Systems and methods of applying disposable gloves without increasing or propagating contamination is, therefore, greatly desired.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to glove application systems for applying disposable gloves and, more particularly, to touchless glove application systems designed to minimize the potential for contamination of the exterior of the gloves during glove application (placement).

The automated glove application systems described herein enable "touchless" self-donning (installation) of disposable gloves and thereby minimize or eliminate user contact with the external surfaces of the glove during the application process. The systems and methods discussed herein can enhance aseptic technique and increase the speed of glove application, while simultaneously preventing contamination associated with user error and inadvertent contaminating contact with the gloves. The glove application systems incorporate individually packaged and sterilized gloves that can be accessed by the user via an automated system. In some embodiments, individually packaged gloves may be provided in a pre-packaged, sterilized cartridge assembly that can easily be installed into the dispenser systems described herein. In one or more disclosed embodiments, the glove application systems described herein utilize a pressure system that provides cyclical negative and positive pressure conditions that aid in glove application and fitting the glove to the hand of a user.

The presently-disclosed embodiments are advantageous in view of the current COVID-19 pandemic. In particular, personal protective equipment (PPE), such as disposable gloves, is prone to rapid contamination and is typically discarded once contaminated, either on purpose or inadvertently. The automated glove application systems described herein can help reduce the amount of wasted disposable gloves that may be accidentally compromised, which would otherwise require the user to discard the contaminated glove and don or apply a new glove. The embodiments disclosed herein may be particularly advantageous in settings where a high degree of sanitation or sterilization is required or desired such as, but not limited to, hospitals, nursing homes, restaurants, bathrooms, etc. As used herein, the terms "don" and "donning" refer to the act of applying or installing a glove on a hand. The terms "don" and "donning" may be interchangeably used with terms such as "apply" or "install".

Figure 1:
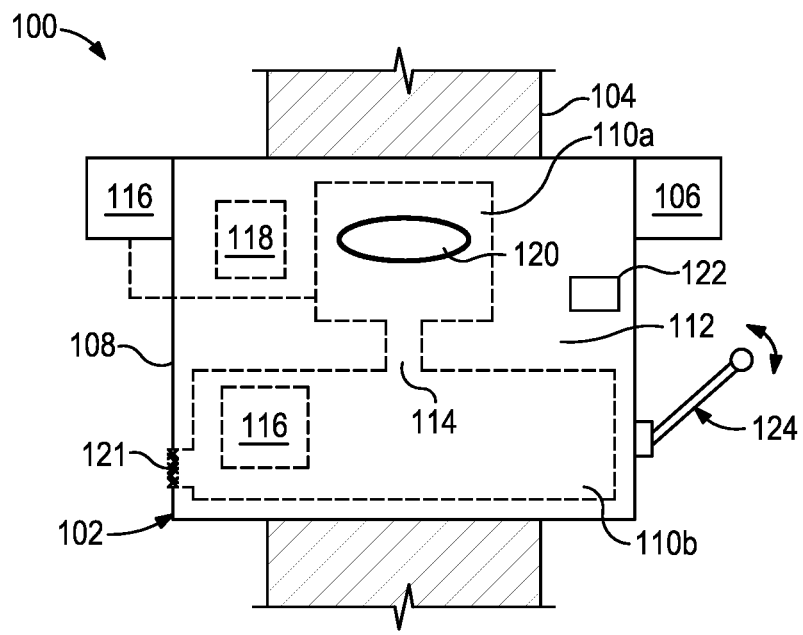
FIG. 1 is a front view an example glove application system, according to one or more embodiments.

FIG. 1 is a front view of an example glove application system 100, according to one or more embodiments. As illustrated, the glove application system 100 (hereafter "the system 100") may include a glove application module 102. In some embodiments, the glove application module 102 may comprise a standalone system that may be portable to any desired location. In other embodiments, however, the glove application module 102 may be mounted to a rigid structure 104 for use. The rigid structure 104 may comprise a variety of stationary structures such as, but not limited to, a wall, a countertop, a stand, a public access point (e.g., a gas pump, a subway entrance, an elevator wall, etc.), or any combination thereof. Alternatively, the rigid structure 104 may comprise a movable (transportable) structure, such as a wheeled cart, an emergency vehicle, or any combination thereof.

In some embodiments, a source of power may be included with the rigid structure 104 to operate the glove application module 102, such as electrical grid power available through a wall power outlet (e.g., 110V), or electrical power derived from a vehicle power port, etc. In embodiments where the glove application module 102 is affixed to a piece of equipment, such as a gas pump, an elevator, etc., the electrical power may be derived from such equipment. Alternatively, or in addition thereto, the glove application module 102 may include a localized power source 106, such as one or more batteries (e.g., 12V, 24V, etc.), fuel cells, a solar panel power system, or any combination thereof.

The glove application module 102 includes a housing 108 that contains or supports various devices or mechanisms used to operate the glove application module 102. In some embodiments, the housing 108 provides or otherwise defines a first or "install" cavity 110a and a second or "pressure" cavity 110b separated from the install cavity 110a by a partition 112. The cavities 110a,b may alternately be referred to as "zones". The partition 112 separates the first and second cavities 110a,b but also defines a pressure vent 114 that provides fluid (air) communication between the first and second cavities 110a,b.

The glove application module 102 may also include a pressure system 116 operable to generate cyclical negative and positive pressure conditions in the install cavity 110a. The negative and positive pressures are measured with respect to ambient or atmospheric pressure. Accordingly, negative pressure generation provided by the pressure system 116 may comprise any pressure condition within the install cavity 110a that is lower than atmospheric pressure, and positive pressure generation may comprise any pressure condition within the install cavity 110a that is higher than atmospheric pressure.

In some embodiments, the pressure system 116 (shown in dashed lines) may be arranged within the pressure cavity 110b and may be operable to generate negative and positive pressure conditions in the install cavity 110a via the pressure vent 114. In such embodiments, the pressure system 116 may generate cyclical negative and positive pressure within the pressure cavity 110b, and such pressure changes will be communicated to the install cavity 110a via the pressure vent 114. More specifically, the pressure system 116 may be configured to generate a low pressure condition within the pressure cavity 110b that draws air from the install cavity 110a and into the pressure cavity 110b via the pressure vent 114. The pressure system 116 may then be configured to generate a high pressure condition within the pressure cavity 110b that forces air into the install cavity 110a via the pressure vent 114. In at least one embodiment, the install cavity 110a may be substantially sealed to enhance the effects of the cyclical negative and positive pressure conditions.

Alternatively, the pressure system 116 may communicate directly with the pressure vent 114 via a hose or the like, thus not affecting pressure conditions in the pressure cavity 110b, but only within the install cavity 110a. In other embodiments, however, the pressure system 116 may be arranged outside of the pressure cavity 110b, such as being attached to the exterior of the housing 104. In such embodiments, the pressure cavity 110b may be omitted as unnecessary, and the pressure system 116 may fluidly communicate directly with the install cavity 110a through a sidewall of the housing 104, for example, to generate the negative and positive pressure conditions in the install cavity 110a.

The pressure system 116 can include any suitable compressor, pump, or device capable of increasing and decreasing the pressure within the install cavity 110a. Suitable examples for the pressure system 116 include, but are not limited to, a pressure piston, an air piston, a plunger, a wiper, a collapsible/deformable mechanism (e.g., a bellows, an accordion-type bellows, an expandable bladder, etc.), a reversing compressor or pump, or any combination thereof. In at least one embodiment, the pressure system 116 may comprise a spring-loaded bellows that may be actuated in one direction to create a positive pressure condition, and allowed to revert back to its natural state while creating a negative pressure condition. In some embodiments, air may be drawn in by the pressure system 116 from the exterior of the housing 108 to increase the pressure within the install cavity 110a. In such embodiments, a vent 121 may be defined in a sidewall of the housing 108 and an inlet filter may be arranged within the vent 121 to filter the incoming air. The inlet filter may be a high efficiency particulate air (HEPA) filter configured to trap a variety of contaminants prior to entering the glove application module 102 and, more particularly, the install cavity 110a.

The glove application module 102 may further include a glove cartridge assembly 118 (shown generally in dashed lines) mounted to the housing 108 and including a plurality of individually packaged and releasably secured gloves. The gloves may comprise disposable gloves such as, but not limited to, latex gloves, nitrile gloves, butyl gloves, vinyl gloves, neoprene gloves, or any combination thereof. The gloves may be sterile or non-sterile. As discussed in more detail below, the gloves in the glove cartridge assembly 118 may be individually packaged and/or spaced along a cartridge belt configured to be driven (transferred) between opposing supply and recovery spools. The glove application module 102 may include means for selectively advancing individual gloves in the glove cartridge assembly 118 to align with an access aperture 120 defined in the housing 108. The access aperture 120 provides a location where a user may be able to insert a hand into the install cavity 110a via the access aperture 120 and simultaneously insert the hand into a glove aligned with the access aperture 120.

In some embodiments, as illustrated, the glove cartridge assembly 118 may be arranged within the install cavity 110a. In other embodiments, however, the glove cartridge assembly 118 may be attached to the exterior of the housing 108 and the cartridge belt may be fed into the housing 108 on one side from an externally-mounted supply spool, and received by an externally-mounted recovery spool on an opposing side of the housing 108.

In some embodiments, the glove application module 102 may further include a user interface 122 designed to allow a user to operate the glove application module 102. In some embodiments, the user interface 122 may comprise a touch interface, such as a self-sanitizing switch or button mounted to the housing 108. In such embodiments, a user may manually flip the switch or press the button to activate operation of the glove application module 102, which may cause the glove cartridge assembly 118 to advance the cartridge belt and align a glove with the access aperture 120. In other embodiments, the user interface 122 may comprise a graphical user interface (GUI), such as a self-sanitizing touch-screen display that allows a user to operate the glove application module 102. In such embodiments, the user interface 122 may be programmed to accept user input for various glove selection criteria such as, but not limited to, glove size, glove color, glove material, glove style, right hand, left hand, or any combination thereof.

In yet other embodiments, the user interface 122 may comprise a touchless interface. In such embodiments, for example, the touchless user interface 122 may comprise one or more sensors that facilitate touchless operation of the glove application module 102. More particularly, various sensors incorporated into the glove application module 102 may sense movement or motion in proximity of the user interface 122 (e.g., waving a hand in front of the user interface 122, approaching the glove application module 102, etc.). Such movement or motion in proximity of the user interface 122 may cause the glove cartridge assembly 118 to advance and align a glove with the access aperture 120. Suitable sensors for the user interface 122 include, but are not limited to, motion sensors (e.g., infrared (IR) sensors), photoelectric sensors (e.g., photo eyes), light curtains, light sensors, proximity sensors (e.g., radio-frequency identification (RFID) readers), or any combination thereof. In at least one embodiment, the touchless user interface 122 may comprise a proximity sensor employing RFID technology, for example, which may detect a user's identification (e.g., a company badge or the like) once in proximity of the glove application module 102. In other embodiments, the touchless user interface 122 may comprise a voice-activated computer system with a microphone and speaker(s). In such embodiments, the user may speak voice commands to the user interface 122 to cause the glove cartridge assembly 118 to advance and align a glove with the access aperture 120.

In some embodiments, one or both of the pressure system 116 and the glove cartridge assembly 118 may be powered by the localized power source 106. In other embodiments, one or both of the pressure system 116 and the glove cartridge assembly 118 may be powered with electrical grid power available through a wall power outlet (e.g., 110V), or electrical power derived from a vehicle power port. In yet other embodiments, however, a mechanical actuator 124 may form part of the user interface 122 and may be manually actuated by the user to operate the glove application module 102. Such embodiments may prove advantageous in the event grid power or the localized power source 106 is unavailable, such as in remote or portable applications where ready access to electrical power may be limited.

The mechanical actuator 124 may comprise, for example, one or more levers or pedals that a user must manually actuate (e.g., reciprocate) to operate the glove cartridge assembly 118 and/or the pressure system 116. In the illustrated embodiment, the actuation system 124 comprises a lever that can be pivoted up or down by a user to operate the glove application module 102. In at least one embodiment, the lever may comprise a "wrist blade" or the like, which comprises a generally flat surface that a user may actively engage with an arm, a wrist, etc. to manually actuate the glove cartridge assembly 118 and/or the pressure system 116 without having to use their hands. In other embodiments, the mechanical actuator 124 may comprise a treadle having a geared and/or pulley interconnection with one or both of the glove cartridge assembly 118 and the pressure system 116, and user actuation (operation) of the treadle may cause the glove cartridge assembly 118 and/or the pressure system 116 to operate.

Example operation of the glove application module 102 is now provided. In some embodiments, a user may activate operation of the glove application module 102 through interaction with the user interface 122 and/or the mechanical actuator 124, as generally discussed above. In such embodiments, operating the user interface 122 (e.g., touch or touchless) and/or the mechanical actuator 124 may cause the glove cartridge assembly 118 to advance a cartridge belt and align a glove with the access aperture 120. Once the glove is aligned with the access aperture 120 (or as the glove is being moved and aligned), the pressure system 116 may be activated to generate negative pressure (e.g., a vacuum) within the install cavity 110a. The generated negative pressure may be sufficient to inflate the aligned glove into the interior of the install cavity 110a, but each glove may be operatively coupled to the cartridge belt such that inflating the glove into the install cavity 110a does not release the glove from the cartridge belt. In other embodiments, however, the user must first penetrate a seal that covers the glove before the glove can be inflated into the install cavity 110a, without departing from the scope of the disclosure.

Once the glove is inflated and extended into the install cavity 110a, the user may extend a hand into the inflated glove via the access aperture 120, at which point the pressure system 116 may cycle (switch—return cycle) from generating negative pressure to generating positive pressure within the install cavity 110a. Cycling the pressure system 116 from negative to positive pressure generation may be manually or electronically controlled. In embodiments where the pressure system includes a reciprocating device, such as a spring-loaded bellows, an air piston, or a treadle, cycling the pressure system 116 from negative to positive pressure generation may naturally occur during operation. In some embodiments, the duration of the negative/positive pressure cycle may be based on a selected timing, such as every 2 seconds, 3, seconds, 5 seconds, etc. In other embodiments, cycling the pressure system 116 from negative to positive pressure may be triggered by operation of one or more internal sensors that detect the presence of the hand. In such embodiments, a motion sensor or a light curtain may cause the pressure system 116 to switch (cycle) from negative to positive pressure within the install cavity 110a once the presence of a hand within the inflated glove is detected. In some embodiments, the pressure system 116 may continuously operate, either cycling between negative and positive pressure conditions, or maintaining a negative pressure within the install cavity 110a. In other embodiments, however, the pressure system 116 may only be operated as needed to install a glove, following which operation of the pressure system 116 may cease.

The positive pressure generated by the pressure system 116 may help seat the glove onto the user's hand and thereby provide tactile feedback to the user that the glove is properly donned (installed). Without the positive pressure forces that help seat the glove on the user's hand, a user may be able to withdraw the hand without removing the glove, thus defeating the purpose of the glove application module 102. Accordingly, once the user feels that the glove is properly applied (seated) on the hand from the positive pressure condition, the now-gloved hand may be withdrawn from the access aperture 120. In some embodiments, withdrawing the gloved hand from the access aperture 120 may release the glove from the cartridge belt. In other embodiments, or in addition thereto, the positive pressure condition may create sufficient detachment forces to release the glove from the cartridge belt.

In some embodiments, withdrawing the gloved hand from the install cavity 110a may trigger operation of the glove cartridge assembly 118 to advance and align another glove with the access aperture 120. In such embodiments, the default position for the glove application module 102 may be to have a glove already advanced and aligned with the access aperture 120 before a user approaches the system 100. Accordingly, once a glove is dispensed from the glove application module 102 and the user withdraws the hand, the glove cartridge assembly 118 may automatically advance and align another glove with the access aperture 120, thus readying the glove application module 102 for subsequent and continued use.

Figure 2:
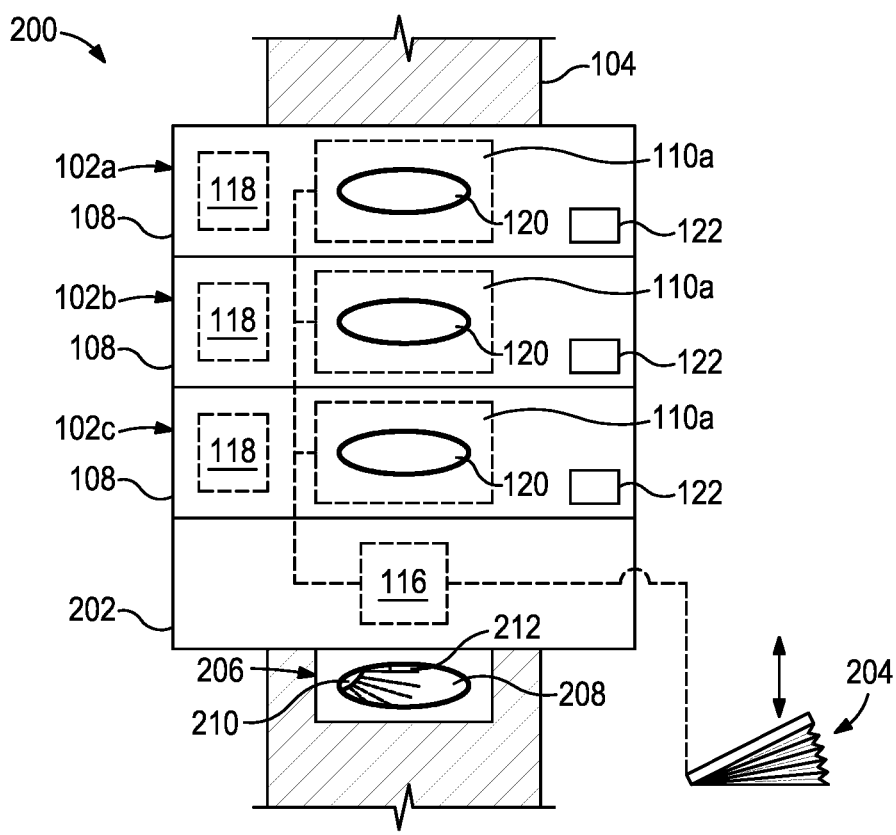
FIG. 2 is a front view another example glove application system, according to one or more additional embodiments.

FIG. 2 is a front view of another example glove application system 200, according to one or more additional embodiments. The glove application system 200 (hereafter "the system 200") may be similar in some respects to the system 100 of FIG. 1 and therefore will be best understood with reference thereto, where like numerals will refer to like components not described again. As illustrated, the system 200 includes a plurality of vertically stacked glove application modules, shown as glove application modules 102a, 102b, and 102c. While three glove application modules 102a-c are depicted in FIG. 2, more or less than three may be employed in the system 200, without departing from the scope of the disclosure. The glove application modules 102a-c may be mounted to the rigid structure 104 for use, or may alternatively comprise a standalone unit.

In some embodiments, each glove application module 102a-c may include a separate housing 108 that contains or supports various devices or mechanisms used to operate the glove application modules 102a-c. In other embodiments, however, the glove application modules 102a-c may share a common housing that incorporates or includes all of the glove application modules 102a-c. Each glove application module 102a-c may provide an install cavity 110a and an access aperture 120 providing a location where the user is able to insert a hand into the corresponding install cavity 110a and simultaneously into an inflated glove aligned with the corresponding access aperture 120.

In some embodiments, the system 200 may further include a mechanical housing 202, which may form part of the housing(s) 108 or may be coupled thereto. The mechanical housing 202 may house the pressure system 116 and various electrical components (e.g., computer systems, etc.) configured to operate the glove application modules 102a-c. In other embodiments, however, the pressure system 116 may alternatively be coupled to the exterior of the housing(s) 108. In such embodiments, the mechanical housing 202 may be replaced with an additional glove application module. The pressure system 116 may be in fluid communication with the install cavity 110a of each glove application module 102a-c. In operation, and depending on user input, the pressure system 116 may be operable to selectively generate cyclical negative and positive pressure in any or all of the install cavities 110a.

Each glove application module 102a-c may further include separate and discrete glove cartridge assemblies 118 (shown in dashed lines) mounted to the housing(s) 108. Each glove cartridge assembly 118 may be pre-packaged and sterilized prior to installation, and may include a plurality of gloves individually packaged and releasably secured to a cartridge belt configured to be driven (transferred) between opposing supply and recovery spools. Each glove cartridge assembly 118 may also be programmed or otherwise operable to selectively advance individual gloves to the corresponding access aperture 120, and depending on user input. More specifically, the system 200 may further include one or more user interfaces 122 (three shown) designed to allow a user to operate the glove application modules 102a-c. In the illustrated embodiment, each glove application module 102a-c includes a separate user interface 122. In such embodiments, each user interface 122 may be configured to trigger operation of the corresponding glove application module 102a-c. In other embodiments, however, the system 200 may include a single user interface 122 configured to selectively operate any of the glove application modules 102a-c, depending on user input.

In some embodiments, each glove application module 102a-c may be configured to dispense a dissimilar type of glove. For example, each glove cartridge assembly 118 may include a different type of glove, and a user may be able to select a desired type of glove by activating operation of the particular glove application module 102a-c via the corresponding user interface 122. The criteria for the different types of gloves that may be dispensed in the system 200 include, but are not limited to, size, color, material, style, right hand, left hand, or any combination thereof.

In some embodiments, the system 200 may further include a mechanical actuator 204 that may be manually actuated by the user to operate one or both of the pressure system 116 and the glove cartridge assemblies 118. In the illustrated embodiment, the mechanical actuator 204 comprises a spring-loaded, foot pedal bellows configured to help operate or replace the pressure system 116. More specifically, the bellows may be pressed down by the user (e.g., with a foot) and subsequently allowed to expand to create cyclical positive and negative pressures within the install cavities 110a. Such embodiments may prove advantageous for remote or portable applications, where ready access to power for the pressure system 116 may be limited.

Operation of the glove application modules 102a-c may be generally similar to the operation of the glove application module 102 of FIG. 1 above, except for the ability to dispense different types of gloves via a plurality of access apertures 120. Moreover, however, in some embodiments, the system 200 may further include an optional sterilization module 206 coupled to or forming part of the housing(s) 108. As illustrated, the sterilization module 206 may provide or define an aperture 208 into which a user can place a gloved hand (or hands) to sanitize and/or sterilize the glove(s). The sterilization module 206 can include a sterilizing device 210 operable to sanitize and/or sterilize the glove(s) upon introduction into the aperture 208. The sterilizing device 210 may include, but is not limited to, an ultraviolet (UV) lamp (e.g., a short-wavelength UV lamp, a UV-C lamp, a germicidal UV lamp, etc.), an ozonator, a chemical disinfectant (e.g., a sprayer, an aerosolizer, a bath, etc.), or any combination thereof. The sterilization module 206 may prove advantageous sterilizing gloves that have been in limited (or longer) use, thus minimizing the need for repeated glove removal and application of new gloves, and thereby helping to reduce wasted PPE.

In some embodiments, the sterilization module 206 may be selectively actuatable via one of the user interfaces 122, thus allowing a user to selectively activate the sterilizing device 210 on demand. In other embodiments, however, the sterilization module 206 may include a sensor 212 (e.g., a proximity sensor) configured to detect the presence of a hand near or within the aperture 208. Once a hand is detected, operation of the sterilizing device 210 may be triggered. In yet other embodiments, operation of the sterilizing device 210 may be continuous and the user need only inert the gloved hand into the aperture 208, without departing from the scope of the disclosure.

Figure 3:
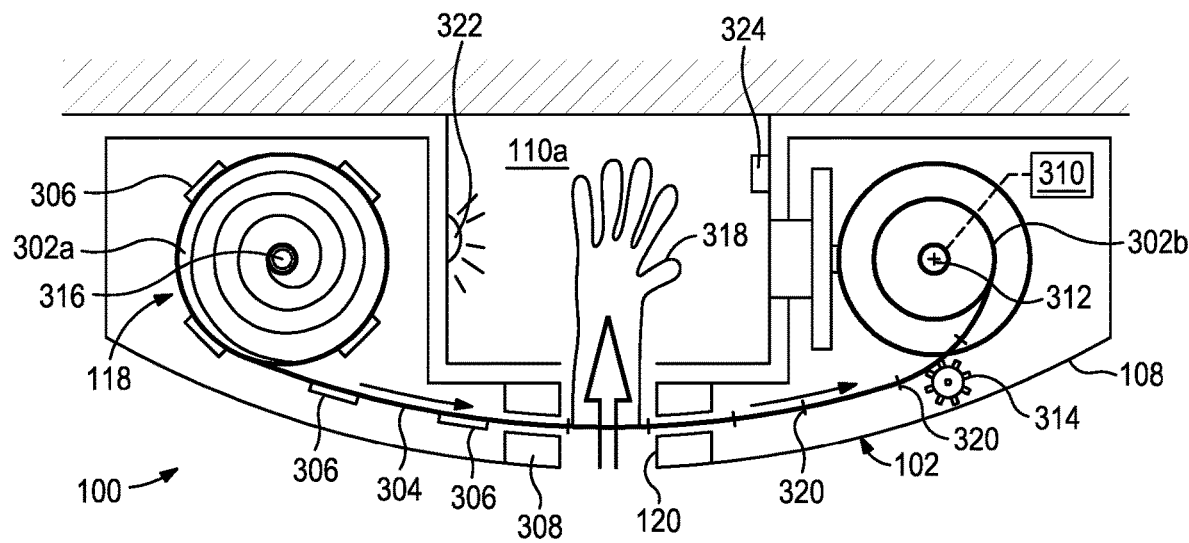
FIG. 3 is an exposed top view of the system of FIG. 1 or 2, according to one or more embodiments of the disclosure.

FIG. 3 is an exposed top view of the system 100 of FIG. 1, according to one or more embodiments of the disclosure. As illustrated, the glove cartridge assembly 118 may include a supply spool 302a, a recovery spool 302b, and a radial cartridge belt 304 extendable between the supply and recovery spools 302a,b. The cartridge belt 304 may be preloaded with a plurality of individually spaced and separated glove cartridges 306 attached to the cartridge belt 304 at predetermined locations and spacing. Each glove cartridge 306 includes a single glove and a means of attaching the glove to the cartridge belt 304. In some embodiments, the glove may be vacuum-packed and sealed within sterilized packaging, but could alternatively not include any packaging and instead merely be attached to the cartridge belt 304. The cartridge belt 304 can have a stipulated number of glove cartridges 306 affixed thereto such as, but not limited to, 25, 50, 100, 200, any number between 25 and 200, less than 25, or more than 200.

Before the glove cartridge assembly 118 is installed in or on the glove application module 102, the cartridge belt 304 may be sterilized and pre-packaged for delivery. In some embodiments, the pre-packaged and sterilized cartridge belt 304 may be entirely (or mostly) pre-wound onto the supply spool 302a, but could alternatively be installed on an existing supply spool 302a forming part of the system 100.

In some embodiments, installing the glove cartridge assembly 118 may entail merely attaching the glove cartridge assembly 118 to the glove application module 102 such that the cartridge belt 304 extends across the access aperture 102. In such embodiments, the glove cartridge assembly 118 may be provided to the user with the cartridge belt 304 already extending between the supply and recovery spools 302a,b. In other embodiments, however, it is contemplated herein that a user will be able to install the glove cartridge assembly 118. In such embodiments, one end of the cartridge belt 304 is pulled radially from the supply spool 302a, extended (threaded) through an alignment guide 308 provided within the housing 108, and operatively coupled to the recovery spool 302b such that driving rotation of the recovery spool 302b will correspondingly pull additional length of the cartridge belt 304 from the supply spool 302a and through the alignment guide 308. As illustrated, the alignment guide 308 is aligned with the access aperture 120, and advancing (pulling) the cartridge belt 304 through the alignment guide 308 will allow individual glove cartridges 306 to be sequentially aligned with the access aperture 120 for operation.

In some embodiments, the recovery spool 302b may be driven in rotation by a motor 310 configured to rotate the recovery spool 302b about a rotational axis 312. In such embodiments, the motor 310 may be operated to advance the cartridge belt 304 through the alignment guide 308 at predetermined increments that accurately and precisely align individual glove cartridges 306 with the access aperture 120. In other embodiments, however, or in addition thereto, the glove application module 102 may further include one or more pinion gears 314 engageable with the cartridge belt 304 and rotatable to advance the cartridge belt 304 through the alignment guide 308 at predetermined increments to align individual glove cartridges 306 with the access aperture 120. In such embodiments, gear teeth of the pinion gear 314 may mate with corresponding holes defined in the cartridge belt 304 such that rotation of the pinion gear 314 drives the gear teeth against the corresponding holes and advances the cartridge belt 314. Moreover, in such embodiments, the recovery spool 302b may not be required, but instead the used portion of the cartridge belt 304 may self-coil on the opposite side of the housing 108 past the pinion gear(s) 314.

Those skilled in the art, however, will readily appreciate that various other ways may be employed to advance the cartridge belt 304, without departing from the scope of the disclosure. For example, as indicated above, in at least one embodiment, a mechanical actuator 124 (FIG. 1) may be included and manually actuated by the user to operate the glove application module 102; e.g., the glove cartridge assembly 118.

In example operation, the cartridge belt 304 is advanced from the supply spool 302a until an individual glove cartridge 306 aligns with the access aperture 120. In some embodiments, the supply spool 302a may be spring loaded and thereby generate constant tension in the cartridge belt 304. In at least one embodiment, for example, the supply spool 302a may include a torsion spring 316 that maintains a tensile load (pull) on the cartridge belt 304 and thereby keeps the cartridge belt 304 taut at all times.

Once a glove cartridge 306 is properly aligned with the access aperture 120, or as the glove cartridge 306 is moving to the access aperture 120, the pressure system 116 (FIGS. 1 and 2) may be operated (activated) to generate negative pressure within the install cavity 110a. The negative pressure may be sufficient to at least partially inflate a glove 318 from the aligned glove cartridge 306 such that the glove 318 extends into the install cavity 110a. The negative pressure required to inflate the glove 318, however, may not be sufficient to release the glove 318 from the cartridge belt 304. In some embodiments, aligning the glove cartridge 306 with the access aperture 120 forms a barrier between the access aperture 120 and the install cavity 110a, and thereby forms a pressure-sensitive seal that helps inflate the glove 318. The glove 318 may be inflated from a packaged (stowed) configuration, which may include a packaged and/or compressed glove with or without an exterior seal or covering.

Once the glove 318 is inflated, the user may extend a hand into the inflated glove via the access aperture 120, and the pressure system 116 may then cycle (switch) to generating positive pressure in the install cavity 110a. As mentioned above, the positive pressure can force the glove 318 against the user's hand and thereby provide positive tactile feedback that lets the user know that the glove 318 is properly donned (applied) and ready to be withdrawn. Once the user feels that the glove 318 is properly applied, the now-gloved hand may be withdrawn from the access aperture 120, thus releasing the glove 318 from the cartridge belt 304. In some embodiments, however, and as also mentioned above, the positive pressure within the install cavity 110a may be sufficient to release of the glove 318 from the cartridge belt 304.

Upon withdrawing the now-gloved hand from the install cavity 110a, the cartridge belt 304 may be advanced until another (subsequent) glove cartridge 306 aligns with the access aperture 120. Alternatively, the cartridge belt 304 may be advanced upon re-activating the glove application module 102. In either scenario, advancing the cartridge belt 304 could be done either manually or through an automated system, as generally described herein. The recovery spool 302b may be configured to collect and/or wind the used cartridge belt 304 and corresponding empty apertures 320 where individual glove cartridges 306 were previously provided. Once the supply spool 302a is depleted of glove cartridges 306, the glove cartridge assembly 118 may be replaced with a new glove cartridge assembly. The glove application module 102 may be configured with interchangeable or refillable glove cartridge assemblies that enable quick refills that minimize potential contamination of the packaged gloves 318. The glove cartridge assembly 118 and any replacement glove cartridge assemblies may come pre-packaged, sterilized, and sealed prior to installation.

In some embodiments, the system 100 may further include a sterilizing device 322 positioned within the install cavity 110a. The sterilizing device 322 may be similar in some respects to the sterilizing device 210 of FIG. 2 and, therefore, may comprise any of the examples given above for the sterilizing device 210. The sterilizing device 322 may be operable to sanitize and/or sterilize the glove 318 upon introduction (inflation) into the install cavity 110a. In some embodiments, operation of the sterilizing device 322 may be activated once the inflated glove 318 is detected within the install cavity 110a with one or more sensors 324 similar to the sensor(s) 212 of FIG. 2.

Figure 4:
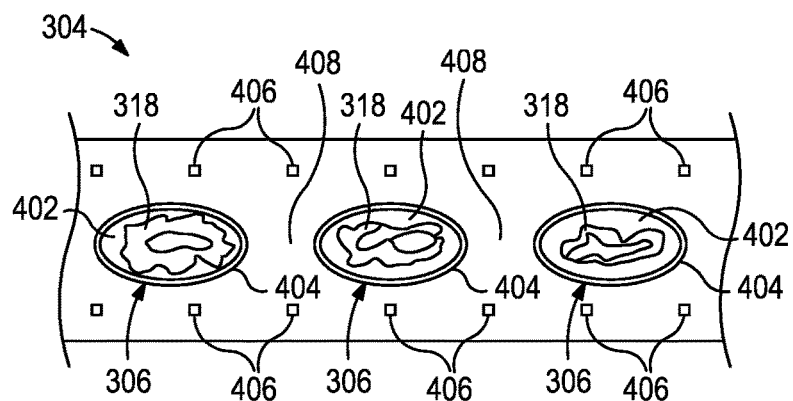
FIG. 4 is a plan view of a portion of an example embodiment of the cartridge belt of FIG. 3, according to embodiments of the present disclosure.

FIG. 4 is a plan view of a portion of an example embodiment of the cartridge belt 304. As illustrated, the cartridge belt 304 may comprise a generally planar strip of material having a plurality of glove cartridges 306 coupled thereto. The cartridge belt 304 may be made of a variety of flexible materials, such as a mechanically durable plastic (e.g., vinyl, polyethylene, etc.), but could alternatively be made of paper or a paper product. In at least one embodiment, however, the cartridge belt 304 may be made of the same material as the gloves 318.

Each glove cartridge 306 may include a glove 318 individually packaged (stowed) and releasably secured to the cartridge belt 304 in the packaged configuration. In some embodiments, each glove 318 may be vacuum packed within a sealed interface 402, such as a protective cellophane seal. In at least one embodiment, the sealed interface 402 may provide tamper proof packaging, but may be thin enough that it will easily tear upon user penetration with a hand. In other embodiments, however, the sealed interface 402 may be omitted. In either scenario, each glove 318 may be sterilized prior to installation on the cartridge belt 304, thus providing a plurality of sealed and sterilized replacement glove cartridges 306 spaced from each other along the cartridge belt 304 at known distances.

Each glove cartridge 306 may further include a fastening system 404 configured to releasably secure the glove 318 to the cartridge belt 304 in the corresponding glove cartridge 306. In some embodiments, for example, the fastening system 404 may be configured to receive and releasably secure the wrist portion of each glove 318 (e.g., the wrist bead), which helps restrain the glove 318 during inflation. In at least one embodiment, the fastening system 404 may comprise a split O-ring that releasably secures the wrist bead of the glove 318. In other embodiments, however, the fastening system 404 may comprise a releasable adhesive, a wax, a Velcro attachment, one or more mechanical staples, or any other type of releasable mechanism that can hold the glove 318 in place until the proper amount of tension is applied on the glove 318 to release it from the fastening system 404. In yet another embodiment, the fastening system 404 may comprise overlaying substrates and the wrist bead of the glove 318 may interpose the overlaying substrates in a sandwich-type arrangement that releasably secures the glove 318. The fastening system 404 may also facilitate a pressurizable seal that allows the glove 318 to be inflated into the install cavity 110a (FIGS. 1-3).

In embodiments where the glove application module 102 (FIG. 3) includes the pinion gear(s) 314 (FIG. 3), the cartridge belt 304 may define a series of equidistantly spaced holes 406 along one or both of its lateral sides. The holes 406 may be configured to mate with the gear teeth of the pinion gear 314 and, as the pinion gear 314 rotates, the gear teeth sequentially engage the holes 406 and thereby advance (drive) the cartridge belt 304 forward. Accordingly, the holes 406 may comprise equidistantly spaced notches or other indexing features configured to aid in the timing and accurate placement of the glove cartridges 306 during operation.

In some embodiments, the cartridge belt 304 may provide or otherwise define spacer sections 408 interposing longitudinally adjacent glove cartridges 306 along the length of the cartridge belt 304. During example operation in accordance with some embodiments, the cartridge belt 304 may be advanced until a spacer section 408 is aligned with the access aperture 120 (FIGS. 1-3). The aligned spacer section 408 may be configured to limit access to the install cavity 110a (FIGS. 1-3) between glove application cycles to minimize contamination. In at least one embodiment, the spacer section 408 may form a seal at the access aperture 120, which may help prevent entry of particulates and contaminants between glove application cycles.

Figure 5:
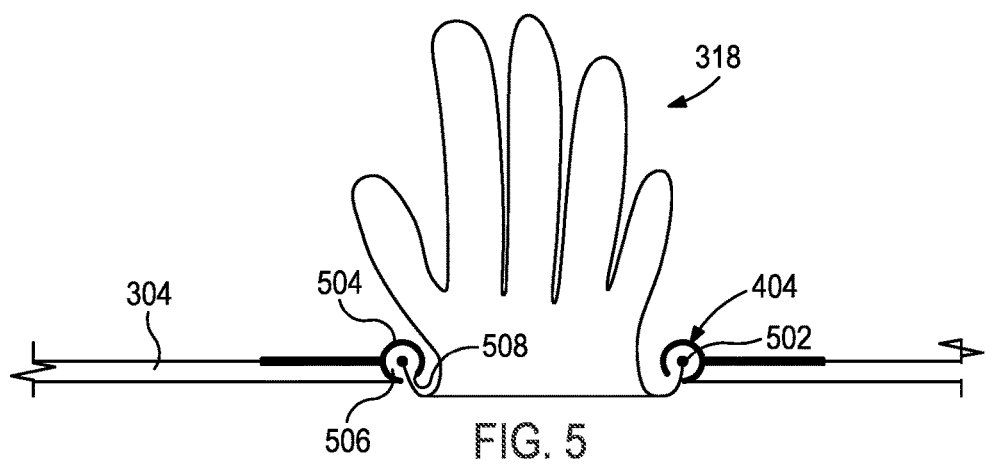
FIG. 5 is a top view of an example inflated glove, according to one or more embodiments.

FIG. 5 is a top view of an example inflated glove 318, according to one or more embodiments. As illustrated, the glove 318 may be releasably coupled to the cartridge belt 304 with the fastening system 404, as generally described above. In the illustrated example, the fastening system 404 may be fixed to the cartridge belt 304 and may be configured to receive and secure a rolled wrist bead 502 of the glove 318.

As illustrated, the fastening system 404 can comprise a split O-ring configured to receive the wrist bead 502 and thereby releasably secure the glove 318 to the cartridge belt 304. More specifically, the split O-ring may comprise a tubular structure 504 that defines an interior 506. In some embodiments, for example, the split O-ring may comprise a length of tubing or hose, and may be made of a variety of materials including, but not limited to, an elastomer, a polymer, or a composite material. The tubular structure 504 may or may not form a complete circle. A split or opening 508 may be defined about the entire tubular structure 504 to enable the wrist bead 502 to be received within the interior 506 to releasably secure the glove 318 to the cartridge belt 304. The tubular structure 504 may be configured to release the wrist bead 502 when the glove 318 receives the hand of a user, when the user withdraws the glove from the install cavity 110a (FIGS. 1-3), or upon experiencing positive pressure within the install cavity 110a.

As will be appreciated, other types of quick-release fastening systems 404 may also be employed including, but not limited to, a frangible seal, a frangible adhesive, a releasable interference fit, a releasable mechanical connection, or any combination thereof. As mentioned above, the attachment force provided by the fastening system 404 may be sufficient such that the negative pressure within the install cavity 110a that inflates the glove 318 does not cause the glove 318 to release from the fastening system 404.

Figure 6A:
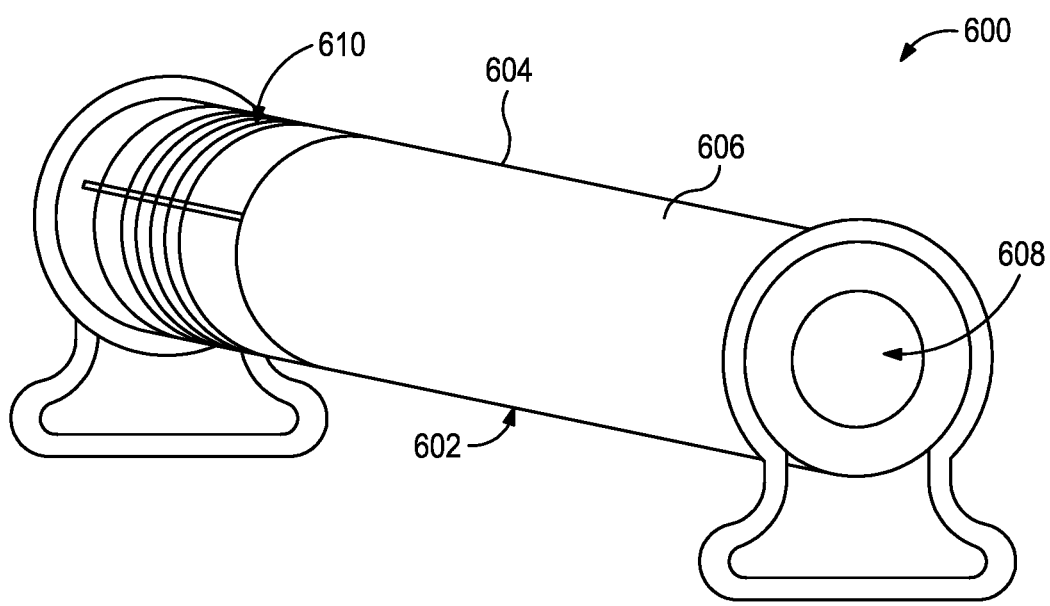
FIG. 6A is an isometric side view of another example glove application system, according to one or more embodiments.

FIG. 6A is an isometric side view of another example glove application system 600, according to one or more embodiments. The glove application system 600 (hereafter "the system 600") may be similar in some respects to the system 100 of FIG. 1. As illustrated, the system 600 includes a glove application module 602 that may comprise a stand-alone, portable system that can be situated on a rigid surface, such as a countertop the like. The glove application module 602 includes a housing 604 that provides or otherwise defines an install cavity 606. In some embodiments, the housing 604 may comprise a cylindrical tube having a circular cross-section, and the install cavity 606 is defined within the tube. Moreover, all or a portion of the housing 604 may be made of a transparent material, such as glass or clear plastic, to enable a user to view the install cavity 606 during operation. An access aperture 608 may be defined or otherwise provided at one end of the housing 604 and provides a location where a user may insert a hand into the install cavity 606 and simultaneously into a glove (not shown) aligned with the access aperture 608.

The glove application module 602 may further include a pressure system 610 operable to generate cyclical negative and positive pressure conditions in the install cavity 606. In at least one embodiment, the pressure system 610 may comprise a collapsible/deformable mechanism, such as a bellows (e.g., accordion-type, spring-loaded, etc.). In example operation, the bellows may be actuated in one direction to create a negative pressure condition within the install cavity 606 and actuated in the opposite direction to create a positive pressure condition within the install cavity 606.

Figure 6B:
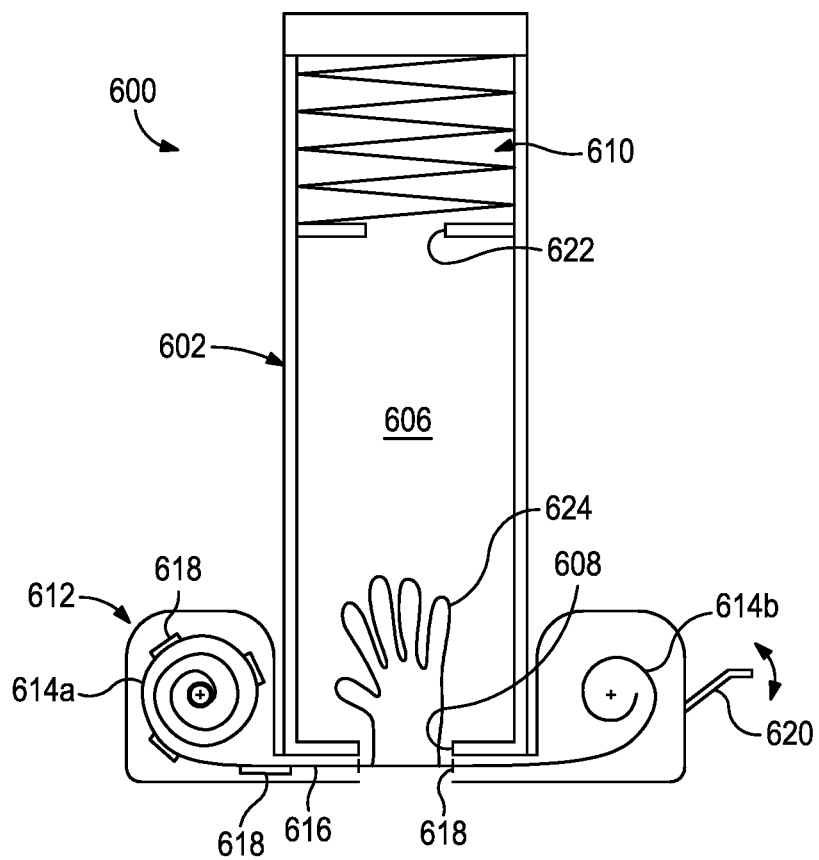
FIG. 6B is a schematic top view of the system of FIG. 6A.

FIG. 6B is a schematic top view of the system 600, according to one or more embodiments. As illustrated, the glove application module 602 may further include a glove cartridge assembly 612 that may be mounted to the housing 604. In some embodiments, the glove cartridge assembly 612 may include a supply spool 614a, a recovery spool 614b, and a radial cartridge belt 616 extendable between the supply and recovery spools 614a,b. Similar to the cartridge belt 304 of FIG. 3, the cartridge belt 616 may be preloaded with a plurality of individually spaced and separated glove cartridges 618 attached to the cartridge belt 616 at predetermined locations and spacing. Each glove cartridge 618 includes a single glove and a means of attaching the glove to the cartridge belt 616.

In some embodiments, the glove cartridge assembly 612 may be installed by attaching the glove cartridge assembly 612 to the glove application module 602 such that the cartridge belt 616 extends across the access aperture 608. In such embodiments, the glove cartridge assembly 612 may be provided to the user with the cartridge belt 616 already extending between the supply and recovery spools 614a,b. In other embodiments, however, it is contemplated herein that a user will install the glove cartridge assembly 612 by pulling one end of the cartridge belt 616 from the supply spool 614a, across (in front of) the access aperture 608, and operatively coupling the end of the cartridge belt 616 to the recovery spool 614b such that driving rotation of the recovery spool 614b will correspondingly pull additional length of the cartridge belt 616 from the supply spool 614a.

Advancing the cartridge belt 616 from the supply spool 614a to the recovery spool 614b will allow individual glove cartridges 618 to be sequentially aligned with the access aperture 608. In some embodiments, the recovery spool 614b may be similar to the recovery spool 302b of FIG. 3 and, therefore, may be driven in rotation by a motor (not shown). In other embodiments, however, one or more pinion gears (not shown) may advance the cartridge belt 616 to align individual glove cartridges 618 with the access aperture 608. In yet other embodiments, the system 600 may include a mechanical actuator 620, such as a wrist blade or ratchet lever that may be manually actuated by the user to operate the glove application module 602 and otherwise advance the cartridge belt 616. In some embodiments, actuating the mechanical actuator 620 may also initiate operation of the pressure system 610.

In example operation, the cartridge belt 616 is advanced from the supply spool 614a until an individual glove cartridge 618 aligns with the access aperture 608. Once a glove cartridge 618 is properly aligned with the access aperture 608, or as the glove cartridge 618 is moving to the access aperture 608, the pressure system 610 may be operated (activated) to generate negative pressure within the install cavity 606. Similar to the pressure system 116 of FIGS. 1 and 2, the pressure system 610 may be automated or otherwise powered using a mechanical actuator (e.g., a spring-loaded, foot pedal bellows) that is manually actuated by the user.

In at least one embodiment, the pressure system 610 may communicate with the install cavity 606 via a pressure vent 622. The negative pressure generated by the pressure system 610 may be sufficient to inflate a glove 624 from an aligned glove cartridge 618 such that the glove 624 extends into the install cavity 606. Once the glove 624 is inflated, the user may extend a hand into the inflated glove via the access aperture 608. In embodiments where the housing 604 is made of a transparent material, the user may be able to view this process and see where the hand is being inserted. The pressure system 610 may then cycle (switch) to generating positive pressure in the install cavity 606, which may force the glove 624 against the user's hand and thereby provide positive tactile feedback. The positive pressure may also be sufficient to release of the glove 624 from the cartridge belt 616. The user may then withdraw the now-gloved hand.

Figure 7A:
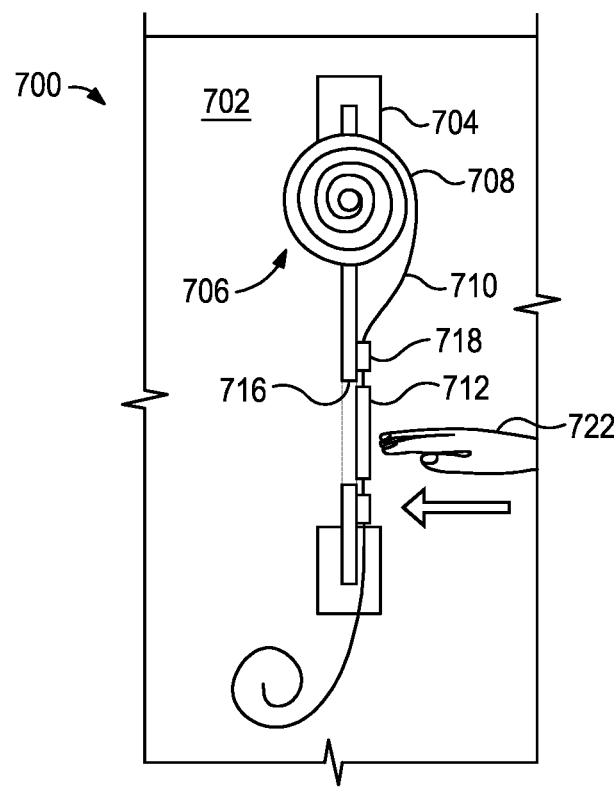
FIGS. 7A and 7B are side and front schematic views, respectively, of another example glove application system, according to one or more embodiments.
Figure 7B:
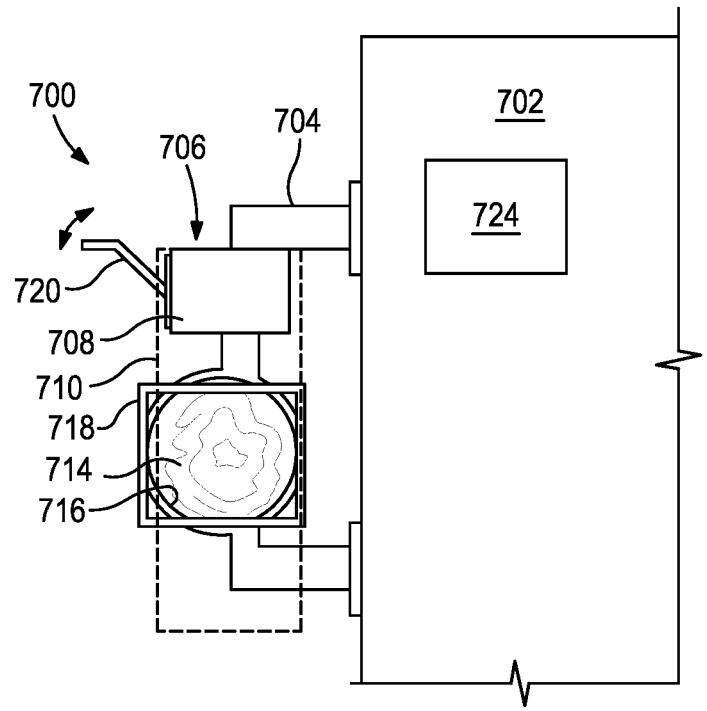

FIGS. 7A and 7B are side and front schematic views, respectively, of yet another example glove application system 700, according to one or more embodiments. Similar to the other glove application systems described herein, the glove application system 700 (hereafter "the system 700") may be configured to sequentially and systematically dispense and don (apply) disposable gloves. Unlike the prior disclosed systems, however, the system 700 does not require the use of a pressure system, or cyclical positive and negative pressure conditions.

In some embodiments, as illustrated, the system 700 may be mounted to a rigid structure 702, such as a gas pump, a subway entrance, a restroom wall, or any other location where rapid and discrete disposable glove dispensing may be desired. In some embodiments, the system 700 may include a mounting bracket 704 that may secure the system 700 to the rigid structure 702 in a desired orientation. The mounting bracket 704 may be fixed to the rigid structure 702 using one or more mechanical fasteners or an adhesive, for example.

As illustrated, the system 700 may include a glove cartridge assembly 706 that may be mounted to the mounting bracket 704. In some embodiments, the glove cartridge assembly 706 may form an integral part of the system 700. In other embodiments, however, the glove cartridge assembly 706 may alternatively comprise a pre-packaged and sterilized container including a supply of disposable gloves that can be mounted to the system 700 (e.g., the mounting bracket 704). In such embodiments, when the supply of gloves is depleted from the glove cartridge assembly 706, the glove cartridge assembly 706 may be detached from the system 700 and replaced with a new glove cartridge assembly.

In some embodiments, the glove cartridge assembly 706 may include a supply spool 708 and a radial cartridge belt 710 (shown in dashed lines in FIG. 7B) wound onto the supply spool 708. The cartridge belt 710 may be preloaded with a plurality of individually spaced and separated glove cartridges 712 (FIG. 7A) attached to the cartridge belt 710 at predetermined locations and spacing. Each glove cartridge 712 includes a single glove 714 (FIG. 7B) and a means of attaching the glove 714 to the cartridge belt 710; e.g., the fastening system 404 of FIGS. 4 and 5. In at least one embodiment, for example, each glove 714 may be attached to the cartridge belt 710 using the split O-ring embodiment described with reference to FIG. 5.

To install the glove cartridge assembly 706, one end of the cartridge belt 710 may be pulled radially from the supply spool 708 and across (in front of) an access aperture 716 provided by the mounting bracket 704. In at least one embodiment, the cartridge belt 710 may be extended (threaded) through an alignment guide 718 attached to the mounting bracket 704 and configured to align successive glove cartridges 712 with the access aperture 716. As illustrated, the alignment guide 718 is aligned with the access aperture 716, and advancing (pulling) the cartridge belt 710 through the alignment guide 718 will allow individual glove cartridges 712 to be sequentially aligned with the access aperture 716 for operation.

In some embodiments, the system 700 may include a recovery spool (not shown) where the used cartridge belt 710 may be wound after dispensing its gloves 714. In other embodiments, however, the recovery spool may be omitted and the used cartridge belt 710 may alternatively collect (e.g., self-coil) at the bottom of the system 700. In such embodiments, portions of the used cartridge belt 710 may be severed or removed from time to time. The cartridge belt 710 may include, for example, pre-perforated tear lines defined in the cartridge belt 710 at predetermined locations, and the cartridge belt 710 may be severed at the tear lines.

In some embodiments, the system 700 may be motorized and otherwise powered to advance the cartridge belt 710 through the alignment guide 718 at predetermined increments that accurately and precisely align individual glove cartridges 712 with the access aperture 716. In such embodiments, the power required to operate the system 700 may be derived from the rigid structure 702. In other embodiments, however, the system 700 may be manually actuated by the user. In such embodiments, the system 700 may include a mechanical actuator 720 that may be manually manipulated by a user to advance the cartridge belt 710 until a glove cartridge 712 aligns with the access aperture 716. In the illustrated embodiment, the mechanical actuator 720 comprises a wrist blade or ratchet lever that a user may engage with a hand, wrist, or forearm to manually advance the cartridge belt 710. In such embodiments, the gearing and/or mechanics of the mechanical actuator 720 may be designed such that with each actuation cycle of the mechanical actuator 720 a new glove cartridge 712 is advanced and aligned with the access aperture 716.

In example operation, the cartridge belt 710 is advanced from the supply spool 708 until an individual glove cartridge 712 aligns with the access aperture 716 at the alignment guide 718. Once the glove cartridge 712 is properly aligned with the access aperture 716, the user may extend a hand 722 (FIG. 7A) into the glove cartridge 712 via the access aperture 716 and simultaneously into the glove 714 packaged in the glove cartridge 712. The act of extending the hand 722 into the glove cartridge 712 causes the glove 714 to expand from its stowed configuration and be received onto the hand 722. Moreover, in some embodiments, extending the hand 722 into the glove 714 may release the glove 714 from the cartridge belt 710. More specifically, extending the hand 722 into the glove 714 provides over pressure that releases the glove 714 from the means of attaching the glove 714 to the cartridge belt 710; e.g., the fastening system 404 of FIGS. 4 and 5. The now-gloved hand 722 may then be withdrawn from the access aperture 716.

In some embodiments, the system 700 may further include a user interface 724 (FIG. 7B) designed to allow a user to operate the system 700. In embodiments where the system 700 is attached to a gas pump, the user interface 724 may be the same interface used to operate the gas pump. In such embodiments, the user interface 724 may be in communication with the system 700 and may comprise any of the touch or touchless configurations described for the user interface 122 of FIGS. 1-2.

In some embodiments, the system 700 may be operable to dispense a glove for a fee. In such embodiments, the user interface 724 may be used to handle user payments and trigger operation of the system 700 once the proper fee has been rendered. In other embodiments, however, the user interface 724 may form an integral part of the system 700, without departing from the scope of the disclosure.

Figure 8:
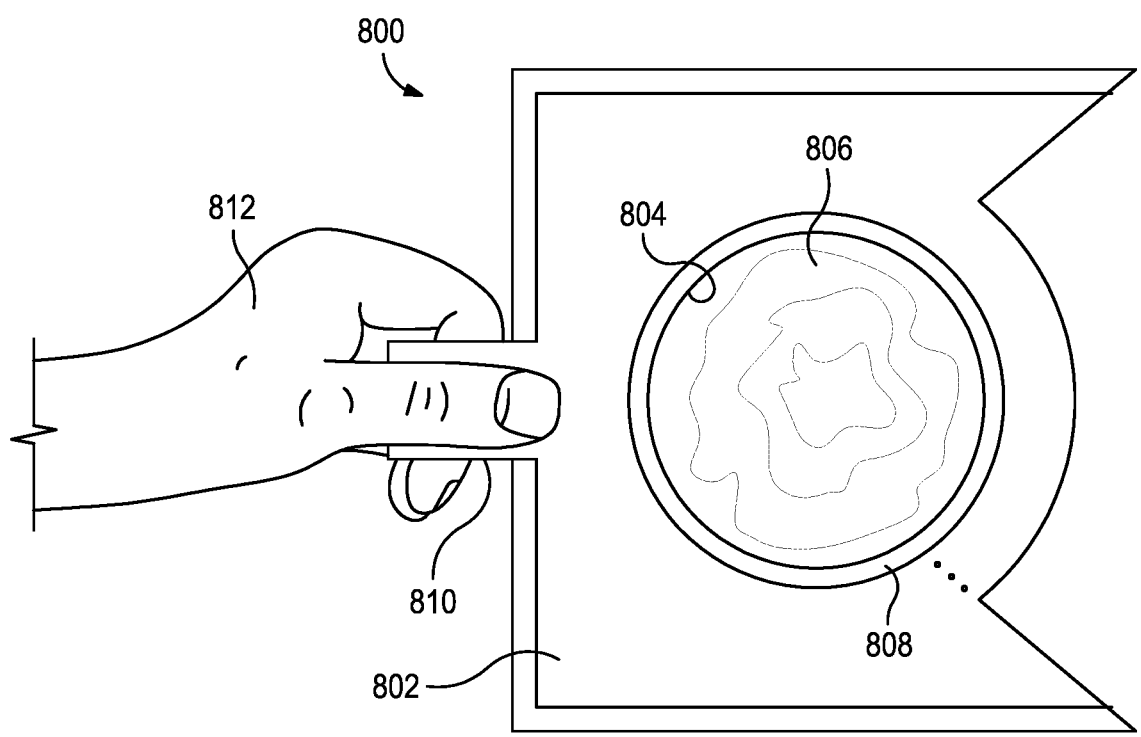
FIG. 8 is a side schematic view of another example glove application system, according to one or more additional embodiments.

FIG. 8 is a side schematic view of yet another example glove application system 800, according to one or more additional embodiments. The glove application system 800 (hereafter "the system 800") may be configured to provide a user with a means of donning (installing) a single glove without contaminating the glove. As illustrated, the system 800 includes an applicator 802 that defines an aperture 804, and a glove 806 is releasably mounted to the applicator 802 at the aperture 804 with a fastening system 808. The applicator 802 may comprise a generally planar structure made of a rigid or semi-rigid material such as, but not limited to, cardboard, cardstock, a plastic, a composite material, a metal, or any combination thereof. In some embodiments, the applicator 802 may be disposable after use, but could alternatively be reusable or recyclable.

While the applicator 802 is depicted in FIG. 8 as exhibiting a particular shape or design, the shape of the applicator 802 may vary, without departing from the scope of the disclosure, and as long as the applicator 802 is large enough to accommodate the glove 806 and the fastening system 808. In some embodiments, for example, the applicator 802 may exhibit a substantially rectangular or square shape, or any other polygonal shape. In other embodiments, the applicator 802 may exhibit a generally circular, oval, or ovoid shape.

As shown in FIG. 8, the system 800 may be provided to the user with the glove 806 in a packaged (stowed) configuration. In the stowed configuration, the glove 806 may be compressed or flattened to about the thickness of the applicator 802, and may or may not include an exterior seal or covering.

The fastening system 808 may be similar to any of the fastening systems described herein and configured to releasably secure the glove 806 to the applicator 802. In at least one embodiment, for instance, the fastening system 808 may comprise a type of split O-ring fastening system similar to the embodiment described with reference to FIG. 5. In other embodiments, however, the fastening system 808 may comprise a releasable or frangible adhesive or seal, without departing from the scope of the disclosure. The fastening system 808 may secure the glove 806 to the applicator 802 until a user inserts a hand into the glove 806 with enough force to release the glove 806 from the applicator 802.

In some embodiments, the applicator 802 may provide or define a tab 810 that provides a location where a user may grasp the applicator 802 in preparation for donning (installing) the glove 806. In other embodiments, however, the tab 810 may be omitted and the user may simply grasp a portion of the applicator 802 to don the glove 806.

In example operation, the user grasps the applicator 802 at the tab 810 (or another portion of the applicator 802) with one hand 812 and simultaneously inserts the other hand (not shown) into the glove 806 at the aperture 804. The user advances the other hand through the aperture 804 and into the glove 806 until sufficient tension is applied on the glove 806 to release it from the fastening system 808. Once the glove 806 is released from the applicator 802, the user may remove the now-gloved hand and dispose of the applicator 802 as appropriate (e.g., trash or recycle). In some applications, the user can repeat the donning process for the first hand 812 using a new system 800 and a new glove 806 and thereby install the new glove 806 on the first hand 812.

In some embodiments, the glove 806 may remain attached to the applicator 802 for use. More specifically, in some cases, it may be desired to have the applicator 802 remain at or near a user's wrist to operate as a type or guard or shield. For example, the applicator 802 may shield the user from splashes or droplets of fuel while using a gas pump. In such embodiments, the user may advance the hand through the aperture 804 and into the glove 806, but not far enough to release the glove 806 from the applicator 802. When it is desired to remove the glove 806, the user can grasp the applicator 802 again (e.g., at the tab 810 or another portion of the applicator 802) and draw the hand out of the glove 806.

It is contemplated herein that the system 800 may be available to users in a package or device that contains a plurality of systems 800. In such embodiments, the tab 810 of each system 800 may be easily accessible by the user to remove a given system 800 from the plurality. In at least one embodiment, for example, a plurality of the systems 800 may be arranged in a stacked relationship and dispensed from a manual or automated dispensing machine (not shown) that sequentially dispenses a new system 800 upon removal of the prior system 800. In other embodiments, the systems 800 may be stacked within a static dispenser (not shown), such as a box, and the user may be able to access the systems 800 within the static dispenser as needed.

It is also contemplated herein that the system 800 may form an integral piece or part of any of the systems 100, 200, 300, 600, or 700 described herein. More specifically, in some embodiments, a plurality of the systems 800 may be coupled to a cartridge belt and spaced from each other to form corresponding glove cartridges, or the plurality of systems 800 may alternatively be attached side-by-side to form the cartridge belt itself. The cartridge belt may then be sequentially advanced to align a given glove 806 with an install cavity and operation of a pressure system may be triggered to inflate the glove 806 into the install cavity.

Embodiments disclosed herein include:

A. A glove application system that includes a glove application module providing a housing that defines an install cavity and an access aperture providing access into the install cavity, a pressure system operable to generate negative pressure and positive pressure in the install cavity, and a glove cartridge assembly mounted to the housing and including a cartridge belt having a plurality of glove cartridges spaced along the cartridge belt, each glove cartridge having a glove releasably secured to the cartridge belt, wherein the glove cartridge assembly is operable to advance the cartridge belt and sequentially align each glove cartridge with the access aperture, and wherein negative pressure generated by the pressure system causes the glove of an aligned glove cartridge to inflate into the install cavity, and positive pressure generated by the pressure system seats the glove against a hand extended into the glove through the access aperture.

B. A method of donning a glove on a hand, the method including activating a glove application system that includes a glove application module providing a housing that defines an install cavity, and a glove cartridge assembly mounted to the housing and including a cartridge belt having a plurality of glove cartridges spaced along the cartridge belt, each glove cartridge having a glove releasably secured to the cartridge belt. The method further including advancing the cartridge belt to align a glove cartridge with an access aperture defined in the housing and providing access into the install cavity, generating negative pressure in the install cavity with a pressure system and thereby inflating the glove into the install cavity, extending a hand into the glove inflated into the install cavity, generating positive pressure in the install cavity with the pressure system and thereby seating the glove against the hand, and releasing the glove from the cartridge belt.

C. A glove application system that includes a mounting bracket that provides an access aperture, and a glove cartridge assembly mountable to the mounting bracket and including a cartridge belt having a plurality of glove cartridges spaced along the cartridge belt, each glove cartridge having a glove releasably secured to the cartridge belt with a fastening system, wherein the glove cartridge assembly is operable to advance the cartridge belt and sequentially align each glove cartridge with the access aperture, and wherein extending a hand through the access aperture installs a glove from an aligned glove cartridge on the hand and simultaneously releases the glove from the cartridge belt.

Each of embodiments A, B, and C may have one or more of the following additional elements in any combination: Element 1: wherein the pressure system comprises a device selected from the group consisting of a pressure piston, an air piston, a plunger, a wiper, a collapsible/deformable mechanism, a reversing compressor or pump, and any combination thereof. Element 2: further comprising a user interface activatable by a user to operate the glove application module. Element 3: wherein the housing comprises a cylindrical tube having a circular cross-section. Element 4: further comprising a mechanical actuator that is manually actuatable by a user to operate at least one of the pressure system and the glove cartridge assembly. Element 5: wherein the glove application module comprises a first glove application module and the glove cartridge assembly comprises a first glove cartridge assembly, the glove application system further comprising a second glove application module coupled to the first glove application module and providing a housing that defines an install cavity and an access aperture that provides access into the install cavity of the second glove application module, wherein the pressure system is operable to generate negative pressure and positive pressure in the install cavity of the second glove application module, and a second glove cartridge assembly mounted to the housing of the second glove application module and including a cartridge belt having a plurality of glove cartridges spaced along the cartridge belt, each glove cartridge of the second glove cartridge assembly having a glove individually packaged and releasably secured to the cartridge belt of the second glove cartridge assembly, wherein gloves included in the first glove cartridge assembly are of a first type and gloves included in the second glove cartridge assembly are of a second type different from the first type. Element 6: further comprising a user interface activatable by a user to select operation of the first or second glove application modules. Element 7: wherein the glove cartridge assembly comprises a supply spool and a recovery spool, and wherein the cartridge belt is extendable between the supply and recovery spools. Element 8: wherein the glove cartridge assembly is vacuum-packed and sealed within sterilized packaging prior to installation in the housing. Element 9: further comprising a sterilizing device positioned within the install cavity. Element 10: wherein each glove is releasably secured to the cartridge belt with a fastening system selected from the group consisting of a split O-ring, a releasable adhesive, a wax, a Velcro attachment, one or more mechanical staples, overlaying substrates, and any combination thereof.

Element 11: wherein activating the glove application system comprises operating a user interface included in the glove application module. Element 12: wherein activating the glove application system comprises manually actuating a mechanical actuator included in the glove application system. Element 13: further comprising sterilizing an exterior of the glove with a sterilizing device positioned within the install cavity. Element 14: wherein the glove application system further includes a sterilization module coupled to the glove application module, the method further comprising extending the hand with the glove seated thereon into the sterilization module, and sterilizing the glove with a sterilizing device arranged within the sterilization module. Element 15: wherein releasing the glove from the cartridge belt comprises releasing the glove with the positive pressure.

Element 16: wherein the fastening system comprises a split O-ring comprising a tubular structure that defines an interior, and an opening defined in the tubular structure to enable a wrist bead of each glove to be received within the interior to releasably secure the glove to the cartridge belt. Element 17: further comprising a mechanical actuator that is manually actuatable to operate the glove cartridge assembly and advance the cartridge belt. Element 18: further comprising an alignment guide through which the cartridge belt is extended to align the cartridge belt with the access aperture.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

What is claimed is:

1. A glove application system, comprising:
a mounting bracket mountable to a rigid structure and defining an access aperture in a plane perpendicular to a mounting surface of the mounting bracket, the mounting bracket extending laterally from the rigid structure to define an air gap interposing the mounting bracket and the rigid structure at the access aperture; and
a glove cartridge assembly mountable to the mounting bracket and including a cartridge belt having a plurality of glove cartridges spaced along the cartridge belt, each glove cartridge having a glove releasably secured to the cartridge belt with a fastening system,
wherein the glove cartridge assembly is operable to advance the cartridge belt and sequentially align each glove cartridge with the access aperture, and
wherein extending a hand through the access aperture installs a glove from an aligned glove cartridge on the hand and simultaneously releases the glove from the cartridge belt.

2. The glove application system of claim 1, wherein the glove cartridge assembly comprises a pre-packaged and sterilized container including the plurality of glove cartridges.

3. The glove application system of claim 1, wherein the cartridge belt is wound on to a supply spool mountable to the mounting bracket.

4. The glove application system of claim 3, further comprising a recovery spool mountable to the mounting bracket, wherein the cartridge belt is extendable between the supply and recovery spools.

5. The glove application system of claim 1, wherein the fastening system is selected from the group consisting of a split O-ring, an adhesive, a wax, a hook and loop fastener attachment, one or more mechanical staples, overlaying substrates, and any combination thereof.

6. The glove application system of claim 1, wherein the fastening system comprises a split O-ring comprising:
a tubular structure that defines an interior; and
an opening defined in the tubular structure to enable a wrist bead of each glove to be received within the interior to releasably secure the glove to the cartridge belt.

7. The glove application system of claim 1, further comprising an alignment guide through which the cartridge belt is extended to align the cartridge belt with the access aperture.

8. The glove application system of claim 1, wherein the glove cartridge assembly is motorized to advance the cartridge belt.

9. The glove application system of claim 8, further comprising a user interface activatable by a user and configured for automated user operation of the glove cartridge assembly.

10. The glove application system of claim 1, further comprising a mechanical actuator that is manually actuatable to operate the glove cartridge assembly and advance the cartridge belt.

11. The glove application system of claim 10, wherein each manual actuation of the mechanical actuator advances and aligns a new glove cartridge of the plurality of glove cartridges with the access aperture.

12. The glove application system of claim 1, wherein the cartridge belt comprises a single layer of material and the plurality of glove cartridges are coupled to the single layer of material, and wherein the glove in each glove cartridge is unsealed.

* * * * *